US00PP22419P2

(12) United States Plant Patent
Kaagman

(10) Patent No.: US PP22,419 P2
(45) Date of Patent: Dec. 27, 2011

(54) *OSTEOSPERMUM* PLANT NAMED 'TRA TERRA'

(50) Latin Name: *Osteospermum ecklonis*
Varietal Denomination: Tra Terra

(75) Inventor: Pim Kaagman, Andjik (NL)

(73) Assignee: Syngenta Crop Protection AG, Basel (CH)

( * ) Notice: Subject to any disclaimer, the term of this patent is extended or adjusted under 35 U.S.C. 154(b) by 212 days.

(21) Appl. No.: 12/657,383

(22) Filed: Jan. 20, 2010

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

PP14,657 P2 * 3/2004 Hansson ..... Plt./360

OTHER PUBLICATIONS

UPOV ROM GTITM Computer Database, GTI Jouve Retrieval Software 2011/01 Citation for 'Tra Terra'.*

* cited by examiner

*Primary Examiner* — Wendy C Haas
(74) *Attorney, Agent, or Firm* — S. Matthew Edwards

(57) ABSTRACT

A new *Osteospermum* plant named 'Tra Terra' particularly distinguished by the medium to large light-terracotta colored ray florets, early flowering habit, compact and upright plant habit with medium leaves and excellent branching.

1 Drawing Sheet

Latin name of the genus and species of the plant claimed: *Osteospermum ecklonis.*

Varietal denomination: 'Tra Terra'.

BACKGROUND OF THE NEW PLANT

The present invention comprises a new *Osteospermum,* botanically known as *Osteospermum ecklonis,* and hereinafter referred to by the variety name 'Tra Terra.'

'Tra Terra' is a product of a planned breeding program. The new cultivar has medium to large light-terracotta colored ray florets, early flowering habit, compact and upright plant habit with medium leaves and excellent branching.

'Tra Terra' originated from a hybridization made in July 2006 in a controlled breeding environment in Andijk, Netherlands. The seed were sown in September 2006.

The female parent was the unpatented, proprietary plant designated 'O04-214-3' with a terracotta flower color. 'O04-214-3' has a smaller flower size, a lighter flower color and more open plant habit than 'Tra Terra.'

The male parent of 'Tra Terra' was the unpatented proprietary plant designated as 'O04-213-1' with a light cream and blue flower color. 'O04-213-1' has a smaller flowers size and less vigor than 'Tra Terra.'

'Tra Terra' was selected as one flowering plant within the progeny of the stated cross in the January 2007 in a controlled environment in Andijk, Netherlands.

The first act of asexual reproduction of 'Tra Terra' was accomplished when vegetative cuttings were propagated from the initial selection in January 2007 in a controlled environment in Andijk, Netherlands.

BRIEF SUMMARY OF INVENTION

Horticultural examination of plants grown from cuttings of the plant initiated in January 2007, and continuing thereafter, has demonstrated that the combination of characteristics as herein disclosed for 'Tra Terra' are firmly fixed and are retained through successive generations of asexual reproduction.

'Tra Terra' has not been observed under all possible environmental conditions. The phenotype may vary significantly with variations in environment such as temperature, light intensity and day length.

Plant Breeder's Rights for this cultivar were applied for in Canada on Jan. 30, 2009 and in Switzerland on Oct. 29, 2009. 'Tra Terra' has not been made publicly available more than one year prior to the filing of this application.

The following traits have been repeatedly observed and are determined to be basic characteristics of the new variety. The combination of these characteristics distinguishes this *Osteospermum* as a new and distinct variety.

BRIEF DESCRIPTION OF THE PHOTOGRAPHS

The accompanying photographic drawing shows typical flower and foliage characteristics of 'Tra Terra' with colors being as true as possible with an illustration of this type.

Figure 1:
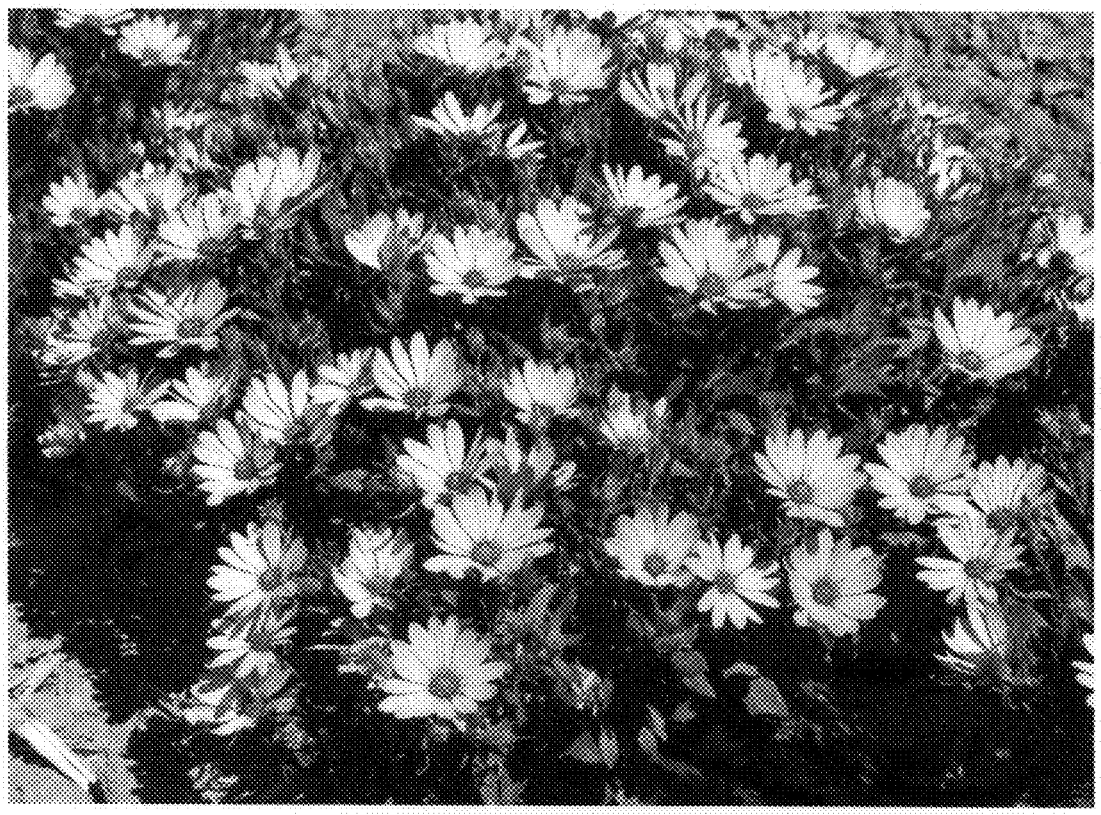
Figure 2:
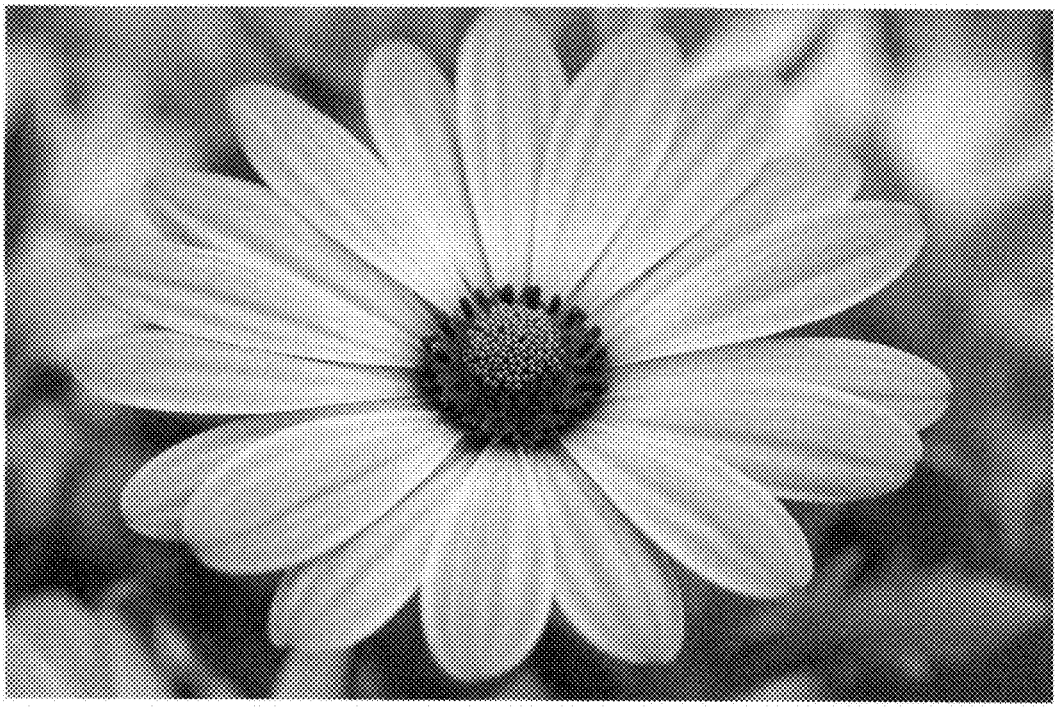

The photographic drawing shows in FIG. 1., a flowering plant of the new variety growing in a outdoor trial field in Gilroy, Calif. in the summer of 2009, and in FIG. 2., a close-up of the flowers.

DETAILED BOTANICAL DESCRIPTION

The plant descriptions, measurements and aforementioned photographs were taken in September 2009 in Gilroy, Calif. under natural light, from plants growing in a outdoor field trial. These plants used in the photograph and descriptions were about 7-8 months old.

Color references are made to The Royal Horticultural Society Colour Chart (R.H.S.) 2001.

TABLE 1

DIFFERENCES BETWEEN THE NEW VARIETY 'TRA TERRA' AND A SIMILAR VARIETY

| | 'Tra Terra' | 'Tra Tercot' (Not patented) |
|---|---|---|
| Branching habit: | More branching | Fewer branching |
| Flower size: | Larger | Smaller |
| Foliage color: | Darker | Lighter |

Plant:

*Form, growth and habit.*—Compact, semi-upright and mounded plant habit. Vigorous habit.

*Plant height.*—About 35 cm.

*Plant height (inflorescence included).*—About 39 cm.

*Plant width.*—About 62-65 cm.

*Garden performance and tolerance to weather.*—Very good.

*Crop time to flowering.*—About 10 weeks.

Roots:

*Number of days to initiate and develop roots.*—24-27 days at about 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137B.

*Lower surface.*—Closest to RHS 137A.

*Mature, leaf color, upper surface.*—Closest to RHS 137B.

*Lower surface.*—Closest to RHS 137A.

*Length.*—3.5-3.7 cm.

*Width.*—1.3-1.4 cm.

*Shape.*—Oblanceolate.

*Base shape.*—Attenuate.

*Apex shape.*—Acute.

*Margin.*—Slightly serrate.

*Texture, upper surface.*—Hirsute.

*Lower surface.*—Hirsute.

*Color of veins, upper surface.*—RHS 144A basally, otherwise indistinct.

*Color of veins, lower surface.*—RHS 144A.

*Petiole color.*—RHS 144A.

*Length.*—1.5-1.7 cm.

*Diameter.*—0.25-0.3 cm.

*Texture.*—Hirsute.

Stem:

*Quantity of main branches per plant.*—5-10.

*Color of stem.*—Between RHS 144A and RHS 144B.

*Length of stem.*—About 35 cm.

*Diameter.*—0.35-0.4 cm.

*Length of internodes.*—1.0-2.0 cm.

*Texture.*—Mostly glabrous.

*Color of peduncle.*—Closest to RHS 146B.

*Length of peduncle.*—4.5-5.5 cm.

*Peduncle diameter.*—0.15-0.2 cm.

*Texture.*—Hirsute with glandular hairs.

Inflorescence:

*Type.*—Daisy-type inflorescence form, held above the foliage, arising from leaf axis, disc and ray florets developing acropetally on a capitulum. Freely flowering habit, numerous inflorescences per plant develop over time.

*Quantity of inflorescences per plant.*—Approximately 50-60.

*Lastingness of individual blooms on the plant.*—11-14 days.

*Fragrance.*—None.

Bud: (Just before opening/showing color)

*Color.*—RHS 150B in the middle with shades of between RHS 165A and RHS 165C at the apex.

*Length.*—0.7-0.8 cm.

*Width.*—1.0 cm.

*Shape.*—Oblate.

Immature inflorescence:

*Diameter.*—3.8 cm.

*Color of ray florets, upper surface.*—RHS 27A base color with vertical stripes of about RHS 166A; RHS between RHS 186C and RHS 181C basally.

*Lower surface.*—RHS N170C base color with stripes of between RHS 166A and RHS 166B.

Mature inflorescence:

*Diameter.*—4.8 cm.

*Depth.*—2.0-2.2 cm.

*Total diameter of 'disc'.*—0.8-0.9 cm.

Ray florets:

*Average quantity of florets.*—About 20 in 1-2 whorls.

*Color of florets, upper surface.*—RHS 27A heavily overlaid with RHS 182D and stripes of about RHS 182C; sometimes has darker apices of RHS 182B; is basally RHS 182 C with a spot of RHS 187B at the very base.

*Lower surface.*—RHS N167C with stripes of between RHS 165A and RHS 165B.

*Length.*—2.4-2.6 cm.

*Width.*—0.6 cm.

*Shape.*—Oblanceolate.

*Apex shape.*—Praemorse.

*Margin.*—Entire.

*Texture, upper surface.*—Papillose; and pilose basally

*Lower surface.*—Papillose; and pilose basally.

Disc florets:

*Average quantity of florets.*—About 75-100.

*Color of florets.*—RHS 158C with RHS 176A apex and margins; sometimes has RHS 176B between the margins.

*Length.*—0.6-0.7 cm.

*Width.*—0.2 cm.

*Shape.*—Tubular, enlongated.

*Apex shape.*—Acute, 5 pointed.

Phyllaries:

*Quantity.*—14-15.

*Color, upper surface.*—Closest to RHS 143C.

*Lower surface.*—Closest to RHS 143C.

*Length.*—0.7-0.9 cm.

*Width.*—0.15 cm.

*Shape.*—Ligulate.

*Apex shape.*—Acute.

*Based.*—Fused.

*Margins.*—Entire.

*Texture, upper surface.*—Hirsute with glandular hairs.

*Lower surface.*—Hirsute with glandular hairs.

Reproductive organs:

*Gynoecium.*—Found on both florets.

*Pistil.*—1.

*Length.*—0.5-0.6 cm.

*Style color.*—RHS 155D.

*Style length.*—0.2 cm.

*Stigma color.*—Between RHS 187A and RHS 187B.
*Androecium.*—Found on only disc florets.
*Stamens.*—4-5.
*Color of filaments.*—RHS 155D.
*Length filaments.*—0.3-0.4 cm.
*Anther color.*—RHS 200B with about RHS 200A apex.
*Anther length.*—0.3-0.35 cm.
*Anther shape.*—Oblong.
*Color of pollen.*—RHS 17A.
*Pollen amount.*—Moderate.
*Fertility/seed set.*—Has not been observed on this hybrid.

Disease/pest resistance: Disease/pest resistance has not been observed on this hybrid.

What is claimed is:

1. A new and distinct variety of *Osteospermum* plant named 'Tra Terra,' substantially as illustrated and described herein.

* * * * *